(12) United States Patent
Li

(10) Patent No.: US 12,076,203 B2
(45) Date of Patent: Sep. 3, 2024

(54) METHOD OF MAKING ABSORBENT INSERTS FOR ABSORBING FLUID IN TOOTH CANALS

(71) Applicant: HEALTHDENT TECHNOLOGY INTERNATIONAL, INC., Las Vegas, NV (US)

(72) Inventor: Nathan Y. Li, Las Vegas, NV (US)

(73) Assignee: Nathan Li, Las Vegas, NV (US)

( * ) Notice: Subject to any disclaimer, the term of this patent is extended or adjusted under 35 U.S.C. 154(b) by 527 days.

(21) Appl. No.: 17/226,046

(22) Filed: Apr. 8, 2021

(65) Prior Publication Data

US 2021/0361384 A1    Nov. 25, 2021

Related U.S. Application Data

(63) Continuation of application No. 16/008,020, filed on Jun. 13, 2018, now abandoned.

(Continued)

(51) Int. Cl.
*A61C 5/50* (2017.01)
*A61C 5/40* (2017.01)
(Continued)

(52) U.S. Cl.
CPC .................. *A61C 5/40* (2017.02); *A61C 5/50* (2017.02); *A61C 19/063* (2013.01); *A61C 19/08* (2013.01); *A61F 13/00987* (2013.01); *A61F 13/00995* (2013.01); *A61F 13/01017* (2024.01); *A61F 13/122* (2013.01); *A61F 13/36* (2013.01); *A61L 15/28* (2013.01); *B29B 11/08* (2013.01); *B29C 43/02* (2013.01); *B29C 43/32* (2013.01); *A61F 2013/15715* (2013.01);
(Continued)

(58) Field of Classification Search
CPC ........... A61C 5/40; A61C 5/50; A61L 15/425; B29C 43/02; A61F 13/00995; Y10S 602/90; C08J 9/36
See application file for complete search history.

(56) References Cited

U.S. PATENT DOCUMENTS 1,469,992 A    8/1922   Card
2,659,935 A *  11/1953  Henry .................. B29C 43/003
                                                    15/244.4

(Continued)

OTHER PUBLICATIONS

International Search Report of Counterpart PCT International Application No. PCT/US2018/037428.

(Continued)

*Primary Examiner* — Jerzi H Moreno Hernandez
(74) *Attorney, Agent, or Firm* — LIU & LIU

(57) ABSTRACT

A method of making an absorbent insert for absorbing fluid in a root canal. Forming a body in a pre-compressed state prior to use, having a matrix of absorbent material. The matrix of absorbent material swells upon absorbing fluid after the body in the pre-compressed state has been inserted into the root canal. In the forming process, a sheet of absorbent material is compressed to form a compressed sheet, which is cut and shaped to form an insert. Cutting and shaping is by using complementary split mold halves which (Continued)

together define a cavity corresponding to the body of the insert and stamping the compressed sheet with the split mold halves to form the body of the insert.

18 Claims, 11 Drawing Sheets

Related U.S. Application Data

(60) Provisional application No. 62/519,129, filed on Jun. 13, 2017, provisional application No. 62/632,394, filed on Feb. 19, 2018.

(51) Int. Cl.
| | |
|---|---|
| *A61C 19/06* | (2006.01) |
| *A61C 19/08* | (2006.01) |
| *A61F 13/00* | (2006.01) |
| *A61F 13/01* | (2024.01) |
| *A61F 13/12* | (2006.01) |
| *A61F 13/36* | (2006.01) |
| *A61L 15/28* | (2006.01) |
| *B29B 11/08* | (2006.01) |
| *B29C 43/02* | (2006.01) |
| *B29C 43/32* | (2006.01) |
| *B29L 31/00* | (2006.01) |
| *A61F 13/15* | (2006.01) |

(52) U.S. Cl.
CPC . *B29K 2995/0068* (2013.01); *B29L 2031/753* (2013.01); *Y10S 602/90* (2013.01)

(56) References Cited

U.S. PATENT DOCUMENTS

| | | | |
|---|---|---|---|
| 2,846,927 A * | 8/1958 | Masci | A61F 13/00987 |
| | | | 433/136 |
| 2,865,283 A * | 12/1958 | Stoffer | C08J 9/36 |
| | | | 15/244.4 |
| 3,018,778 A | 1/1962 | Brilliant | |
| 3,523,535 A | 8/1970 | Croon et al. | |
| 3,932,209 A | 1/1976 | Chatterjee | |
| 4,198,977 A | 4/1980 | Aoki | |
| 4,372,314 A | 2/1983 | Wall | |
| 4,425,094 A | 1/1984 | Tateosian et al. | |
| 4,565,722 A | 1/1986 | Highgate et al. | |
| 4,705,514 A | 11/1987 | Barnard | |
| 7,425,664 B2 | 9/2008 | Maass, Jr. et al. | |
| 8,809,614 B2 | 8/2014 | Wilhoit | |
| 9,144,625 B2 | 9/2015 | Law | |
| 2003/0008264 A1 | 1/2003 | Rubin | |
| 2004/0053201 A1 | 3/2004 | Dovgan | |
| 2006/0142561 A1 | 6/2006 | Luo et al. | |
| 2010/0021528 A1 | 1/2010 | Sackinger et al. | |
| 2011/0143312 A1 * | 6/2011 | McAdams | A61L 15/425 |
| | | | 433/136 |
| 2014/0088529 A1 | 3/2014 | Bengtson | |
| 2014/0315155 A1 | 10/2014 | Li et al. | |
| 2016/0175157 A1 | 6/2016 | Kolb | |

OTHER PUBLICATIONS

European Search Report dated May 22, 2023 issued in Counterpart EP Application No. 22210844.1.

* cited by examiner

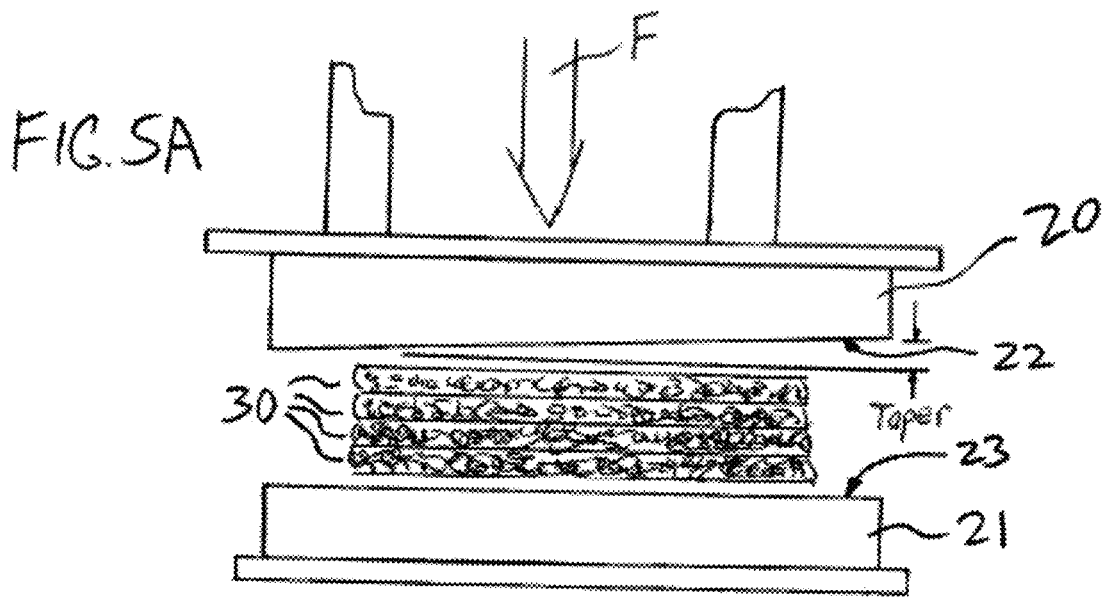
FIG. 5A
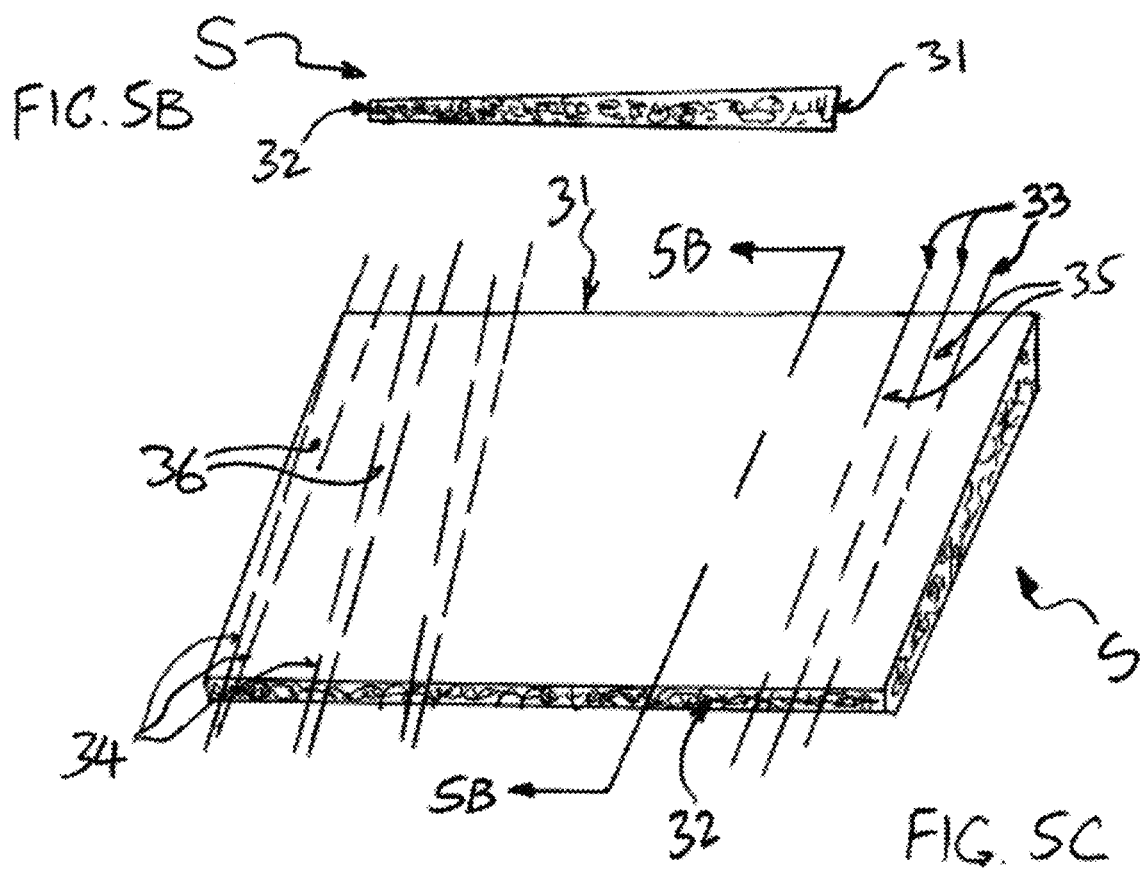
FIG. 5B
FIG. 5C

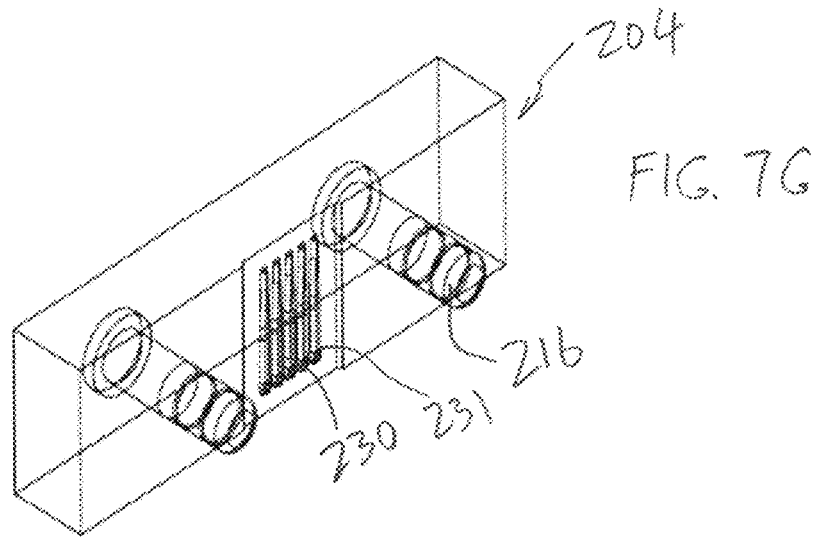
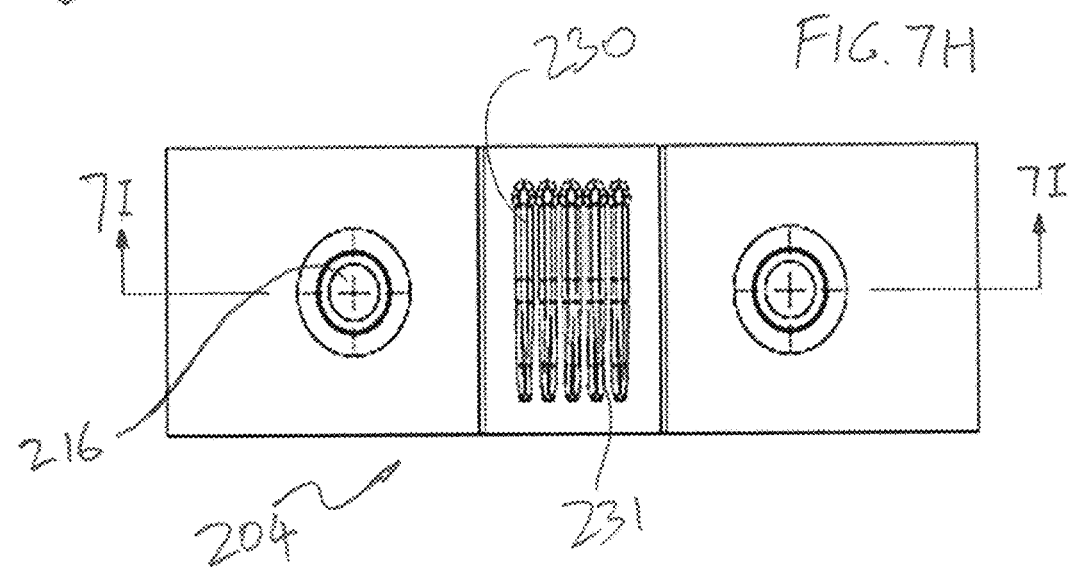
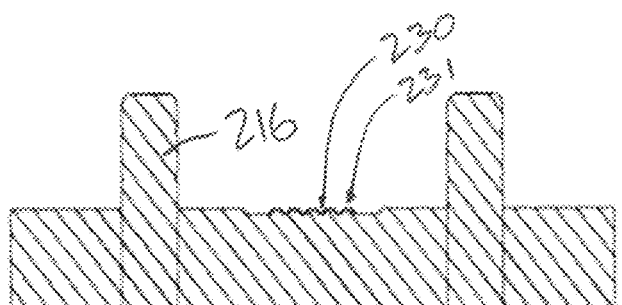

METHOD OF MAKING ABSORBENT INSERTS FOR ABSORBING FLUID IN TOOTH CANALS

1. PRIORITY CLAIM

This application is a continuation of U.S. patent application Ser. No. 16/008,020 filed on Jun. 13, 2018, which claims the priority of: (a) U.S. Provisional Patent Application No. 62/519,129 filed on Jun. 13, 2017; and (b) U.S. Provisional Patent Application No. 62/632,394 filed on Feb. 19, 2018, which are fully incorporated by reference as if fully set forth herein. All publications noted below are fully incorporated by reference as if fully set forth herein.

BACKGROUND OF THE INVENTION

2. Field of the Invention

The present invention is directed to absorbent inserts which are used in tooth cavities (including pulp chambers and root canals).

3. Description of Related Art

Dental root canal treatment basically involves three steps: shaping, cleaning, and obturation. Cleaning step involves chemical solution irrigation and absorbent point drying the root canal space. FIG. 1 is a schematic sectional view of a human tooth (e.g., a molar). As shown, the tooth T has a crown (enamel) portion C protruding above the gum G. As shown, in the shaping step, the crown C has been drilled open to expose the internal tooth cavities, which include a pulp chamber PC below the crown C, and root canal spaces R. After the root canal spaces have been shaped using a file, they are thoroughly cleaned, including removing fluids using fluid absorbent points, to prepare for obturation (filling and sealing with a compatible material).

Today's absorbent point is made of paper therefore it is commonly referred to as "paper point". It is a thin and cone shaped point that comes in different tapers and different sizes. The production process for absorbent point has not been changed over the last 60 years. It is done by manually rolling a wet triangular shaped piece of tissue like paper into a point with a single taper throughout the point. Adhesive such as starch is applied during the rolling process.

Disadvantages of using prior art absorbent inserts made of paper material and manual hand rolling technique (paper points) include:

Product cleanliness is questionable.

Paper fibers on the prior art paper point can separate from the point and drop deep into root canal space to become a potential infection source. As shown in FIGS. 2A and 2B, under a microscope, the surfaces of the prior art paper points are not smooth and clean, and there is presence of flailing materials, which can easily break off and become lodged in the small root canal space.

Prior art paper points do not expand/swell in size after absorbing fluid to completely fill the entire root canal space, which may include irregular fissures in the periphery of the root canal space, hence not be able to thoroughly remove fluid in the root canal space. Further, sizing of prior art paper points is not accurate enough for proper use.

Prior art paper points do not absorb fluid well enough due to the presence of too much adhesive and sealers therein.

Prior art paper points become too soft and loosen up upon fluid absorption, which render difficult to insert them all the way to reach the tip of root canal space.

Manually hand rolled paper absorbent point can have only one or a single continuous taper. Today's root canal treatment technique often requires absorbent point to have multiple tapers.

It is desirable to develop an absorbent insert that is specifically suited for drying the small cavity spaces within a tooth.

SUMMARY OF THE INVENTION

The present invention provides an improved absorbent insert for use in tooth cavities with improved rigidity and absorbent rate, which overcomes the drawbacks of the prior art absorbent points.

In accordance with the present invention, the inventive absorbent insert comprises a compressed absorbent material, which may comprise particles as a filler dispersed therein to improve stiffness/rigidity of the insert and controls the absorbency of the compressed absorbent material, to result in an insert having a desired absorbency and rigidity/stiffness. The fillers may include hydrophilic particles, which further serves to facilitate fluid absorption by the insert. The insert is shaped and sized for inserting into a tooth cavity, such as a pulp chamber or a root canal space. The insert expands or swells upon absorbing fluid within the tooth cavity, so as to more completely dry the tooth cavity.

In one aspect of the present invention, the absorbent insert is applied as an absorbent point to absorb fluid inside a tooth cavity (e.g., to absorb fluid in a root canal to prepare it for filling in a root canal treatment procedure). In another aspect of the present invention, the absorbent insert is applied as an absorbent point that also serves as a substrate of an applicator for medication to be applied to a tooth cavity (e.g., a root canal, a pulp chamber, etc.). The absorbent insert is provided (e.g., coated or impregnated) with a medical agent, which medical agent is released into the tooth cavity as the absorbent material absorbs fluid in the tooth cavity.

The present invention takes into consideration various factors to process known high absorbent materials into desired shape, form, and appropriate rigidity and fluid absorbent rates, to produce absorbent inserts in the form of absorbent points suitable for use in tooth cavities including root canals. Some of the obstacles encountered in utilizing known absorbent materials for root canal absorbent inserts include the requirement of very small size required of an absorbent insert to properly fit into full length of a root canal space, and the requirement to be able to completely remove the absorbent insert from the root canal space without breakage or debris of the absorbent insert in the root canal space. The present invention provides absorbent inserts with improved rigidity and absorbent rate by optimizing extent of compression of absorbent material and addition of filler material (e.g., filler material with hydroxyl group or hydroxyl radical).

As will be explained more fully below, the present invention is direct to an absorbent insert for absorbing fluid in a tooth cavity, comprising a body that comprises a compressed matrix of absorbent material, which is shaped and sized to allow the body to be inserted into a tooth cavity, wherein the tooth cavity comprises at least one of a root canal and a pulp chamber, and wherein the compressed matrix of absorbent material expands or swells upon absorbing fluid in the tooth cavity. In one embodiment, the absorbent material comprises a sponge-like material. The sponge-like material may comprise at least one of polyvinyl alcohol (PVA), polyester, cellulose, hemicellulose, hydrocolloid. The body may further comprise a filler dispersed in the sponge-like material. The material of the filler comprises at least one of Titanium, Silica, Titanium Dioxide, and Zinc Oxide particles.

The body of the absorbent insert has a sectional dimension in the dry state (i.e., before absorbing fluid) that is no larger than in the order of about 10 mm, preferably no larger than 2.0 mm to 3 mm. In general, the body of the absorbent insert is shaped with a generally slender, longitudinal structure. The longitudinal structure may comprise a predefined tapered structure terminating in a small tip end, and wherein the tapered structure of the body is predefined on the body prior to inserting into a dental root canal. The tapered structure may further comprise a plurality of tapered sections along an axial direction of the longitudinal structure of the body, wherein at least two of the tapered sections have different tapers along the axial direction, thereby defining a multi-tapered structure.

In another aspect, the present invention is directed to an absorbent point that applies a medical agent within the root cavity. In the aspect, the body of the absorbent insert comprises a medical agent, wherein the medical agent is released when the absorbent material is exposed to fluid in the tooth cavity. The medical agent is disposed at least at or near an exterior surface of the body (e.g., by coating onto the exterior surface of the body), and/or at least impregnated in the absorbent material.

The medical agent comprises at least an active ingredient that has one of the following effects when applied in the tooth cavity: therapy, treatment, healing, curative, remedial, restorative, tonic, reparative, corrective, antibiotic, anesthetic, disinfect, anti-inflammatory, pain relief. In this regard, the medical agent may comprise at least one of a healing agent, a curative agent, a remedial agent, a restorative agent, a tonic agent, a reparative agent, a corrective agent, an antibiotic agent, an anesthetic agent, a disinfecting agent, a blood clotting agent, a steroidal agent, a hormonal agent, anti-inflammatory agent, a pain-relieving agent. For example, the absorbent insert having medical agent may serve as dressing material for inter pulpal space therapy/treatment purpose.

In a further aspect, the present invention is directed to a method of making an absorbent insert for absorbing fluid in a tooth cavity, comprising forming a body that comprises a compressed matrix of absorbent material, which is shaped and sized to allow the body to be inserted into a tooth cavity, wherein the tooth cavity comprises at least one of a root canal and a pulp chamber, and wherein the compressed matrix of absorbent material expands upon absorbing fluid in the tooth cavity.

The forming step may comprise providing an injection mold having at least a cavity defined in the injection mold corresponding to the shape of the body of the insert; injecting the absorbent material into the cavity in the injection mold; and molding the absorbent material to form the body of the insert, wherein the absorbent material is in a compressed state after injecting in the cavity. The molded insert may be subject to pressing or stamping procedure(s) for further compression.

The forming step may instead comprise providing complementary stamping split mold halves, which together define at least a cavity corresponding to the shape of the body of the insert; placing a sheet of absorbent material between the stamping split mold halves; and stamping the sheet with the stamping split mold halves to form the body of the insert, wherein the absorbent material is in a compressed state after stamping.

The forming step may instead comprise providing a sheet of absorbent material; compressing the sheet of absorbent material; and cutting the sheet of absorbent material to form the body of at least one insert.

The forming step may instead comprise extrusion, liquid molding, and/or rolling processes, which may be followed by additional pressing or stamping procedure(s) for further compressions.

BRIEF DESCRIPTION OF THE DRAWINGS

For a fuller understanding of the nature and advantages of the invention, as well as the preferred mode of use, reference should be made to the following detailed description read in conjunction with the accompanying drawings. In the following drawings, like reference numerals designate like or similar parts throughout the drawings.

FIG. 5A is a schematic side view illustrating compression of an absorbent material in accordance with one embodiment of the present invention; FIG. 5B is a schematic sectional view of the compressed sheet of absorbent material taken along line 5B-5B in FIG. 5C; FIG. 5C is a schematic perspective view of the compressed sheet of absorbent material in accordance with one embodiment of the present invention.

FIG. 7G is a schematic perspective view of the bottom mold halve in FIG. 7A; FIG. 7H is a top view of the bottom mold halve showing the mold chambers; FIG. 7I is a schematic sectional view illustrating the stamp molding mold taken along line 7I-7I in FIG. 7H.

DETAILED DESCRIPTION OF THE PREFERRED EMBODIMENTS

This invention is described below in reference to various embodiments with reference to the figures. While this invention is described in certain embodiments for achieving this invention's objectives, it will be appreciated by those skilled in the art that variations may be accomplished in view of these teachings without deviating from the scope and spirit of the invention.

Figure 1:
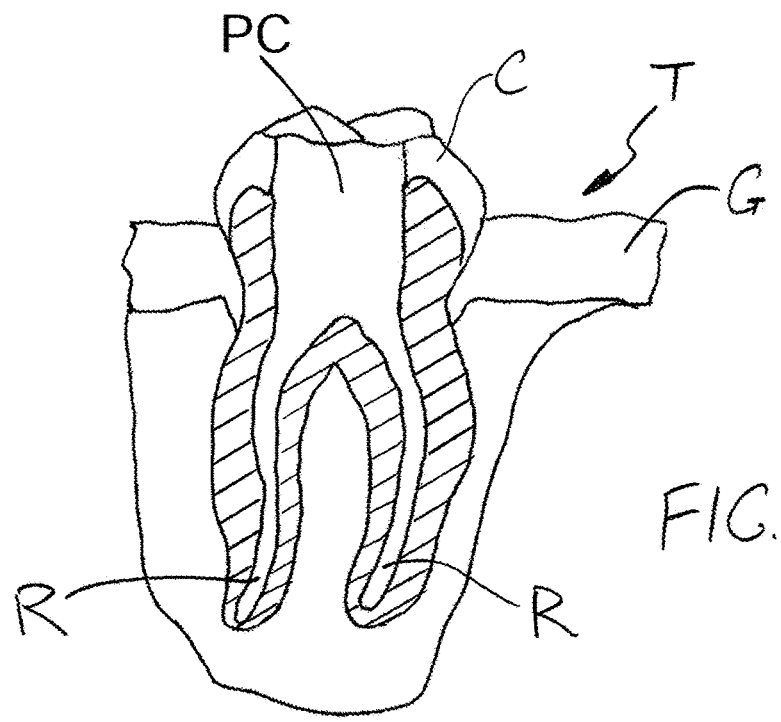
FIG. 1 is a schematic sectional view of a human tooth, showing internal pulp chamber and root canals.

In accordance with the present invention, the inventive absorbent insert comprises a compressed absorbent material that comprises particles as a filler dispersed therein, which improves stiffness/rigidity of the insert, and controls the absorbency of the compressed absorbent material, to result in an insert having a desired absorbency. The insert is shaped and sized for inserting into a tooth cavity (such as a pulp chamber or a root canal space shown in FIG. 1), with acceptable rigidity and absorbent rate.

In one aspect of the present invention, the absorbent insert is applied as an absorbent point to absorb fluid inside a tooth cavity (e.g., to absorb fluid in a root canal to prepare it for filling in a root canal treatment procedure).

In another aspect of the present invention, the absorbent insert is applied as an absorbent point that also serves as a substrate of an applicator for medication to be applied to a tooth cavity (e.g., a pulp chamber). The absorbent insert is impregnated with medication, which is released into the tooth cavity as the absorbent material absorbs fluid in the tooth cavity.

In another aspect of the present invention, the present invention takes into consideration various factors to process known high absorbent materials into desired shape, form, and appropriate rigidity and fluid absorbent rates, to produce absorbent inserts in the form of absorbent inserts suitable for use in tooth cavities including root canals. Some of the obstacles encountered in utilizing known absorbent materials for root canal absorbent inserts include the requirement of very small size required of an absorbent insert to properly fit into full length of a root canal, and the requirement to be able to completely remove the absorbent insert from the root canal space without breakage or debris of the absorbent insert in the root canal space. The present invention provides absorbent inserts with improved rigidity and absorbent rate by optimizing extent of compression of absorbent material and addition of filler material.

In the following disclosure, explanations in connection with the embodiment of the absorbent insert in the form of an absorbent insert are also applicable to the embodiment of the absorbent insert in the form as an applicator, unless otherwise further noted.

Figure 3A:
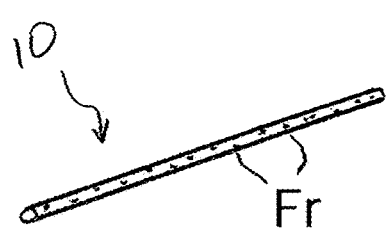
FIG. 3A is a schematic perspective view of an absorbent insert prior to use in accordance with one embodiment of the present invention.
Figure 4A:
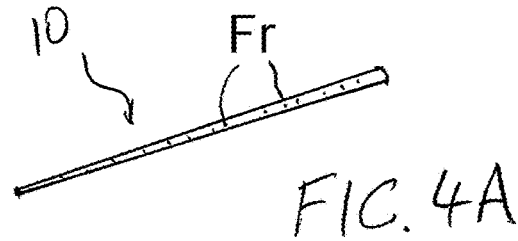
FIG. 4A is a schematic perspective view of an absorbent insert prior to use in accordance with one embodiment of the present invention.

FIGS. 3A and 4A are schematic views of an absorbent insert 10 in accordance with different embodiments of the present invention. In the embodiment of FIG. 3A, the absorbent insert 10 has a generally cylindrical body. In the embodiment of FIG. 4A, the absorbent insert 10 has a generally tapered body (e.g., conical having a circular cross section, or pyramidal having a square cross section).

having a large end and a small tip end (the end to be inserted first into the tooth cavity. The absorbent inserts 10 are shown in FIGS. 3A and 4A in a compressed state prior to use (i.e., prior to inserting into a tooth cavity). In this state, the length of the absorbent inserts 10 can range from 10 mm to 30 mm. The diameter of the cylindrical absorbent insert 10 in FIG. 3A may be in the range of 1.0 mm to 3.0 mm, and the diameters of the tapered absorbent insert 10 in FIG. 3B may be less than 3 mm at the large end, to greater than 0.01 mm at the small tip end. The taper may range from 0 degree to 8 degrees.

The inventive absorbent insert 10 comprises an absorbent material in the form of cellulose fibers, hemicellulose fibers, polyvinyl material, polyester material, or hydrocolloid material, which have pores that are open cell to facilitate fluid absorption. The absorbent material can be bio-inert or bio-compatible. These families of materials have high fluid absorbent rates. These types of materials have similar molecule characteristics, namely, free hydroxyl radicals/groups to attract water molecules (which may include Van der Waals forces). When formed into sponge or sponge-like (hereinafter, collectively referred to as "sponge" or "sponge-like"), fiber matrix, or loose fiber-like texture (i.e., porous matrix of these families of materials, capillary action is present, which increases fluid absorbent ability to a much greater degree). They are used in products such as diapers, tampons, etc. The present invention utilizes the excellent intrinsic absorbent ability of these families of materials in their respective original form, combining them with organic and/or inorganic fillers, to produce the desirable texture for manufacturing and for intended clinical applications—dental root canal disinfection and drying. For purpose of the disclosure of the present invention, the term "sponge" refers to a compressible material that absorbs at least 3 times its own volume of fluid, or expanding/swelling by at least 2 times its own volume. In another embodiment of sponge materials, it absorbs at least 2 times its own weight of fluid.

Figure 3B:
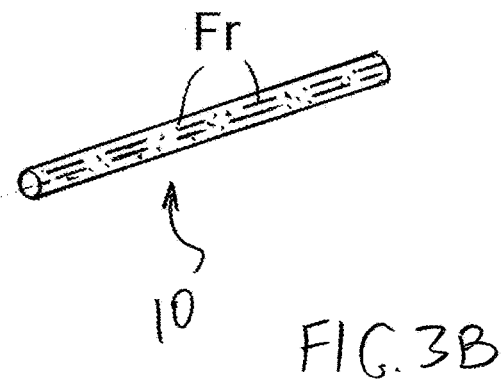
FIG. 3B is a schematic perspective view of the absorbent insert in FIG. 3A after being subject to fluid absorption in accordance with one embodiment of the present invention.
Figure 4B:
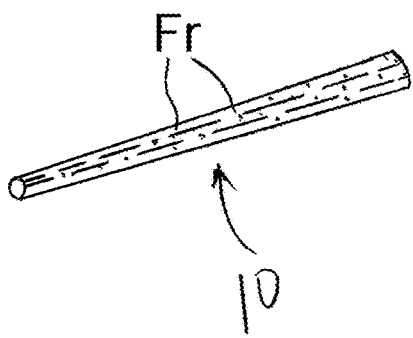
FIG. 4B is a schematic perspective view of the absorbent insert in FIG. 3A after being subject to fluid absorption in accordance with one embodiment of the present invention.
Figure 2A:
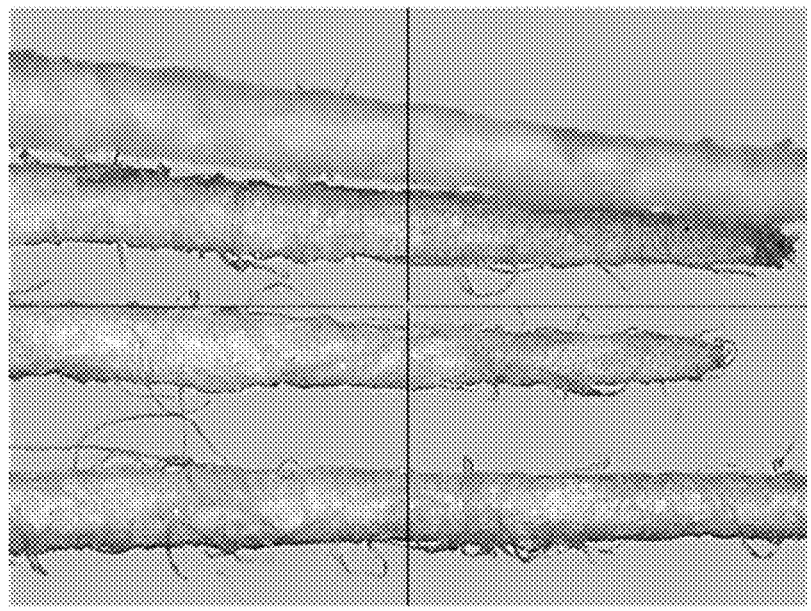
FIG. 2A is an image of a microscopic view of a prior art manual rolled paper absorbent point.
Figure 2B:
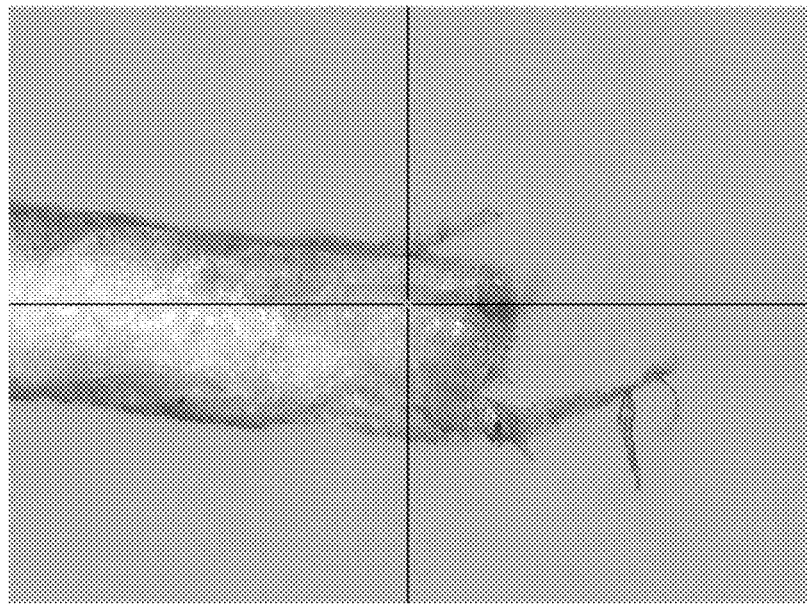
FIG. 2B is an expanded microscopic view of the end tip portion of a prior art manual rolled paper absorbent point.

FIGS. 3B and 4B are schematic views illustrating the corresponding absorbent inserts 10 in FIGS. 3A and 3B in a swelled state, after absorbing fluid (e.g., after inserting the absorbent inserts into tooth cavities).

For absorbent materials comprising these families of fluid absorbent materials configured for medical applicator use, most common form is in sponge form, compressed or non-compressed. Hydrocolloid materials may also be used in gel form and powder form to make into sponge-like structure. When using these materials in sponge form, pore sizes of these materials play a significant role in fluid absorption. It is noted that prior art sponges for medical use have too big pore sizes or too many pores, resulting in too rapid/powerful fluid absorption rate, which would not be suitable for use in tooth cavity.

According to an embodiment of the present invention, optimal pore sizes of the absorbent inserts preferably have diameters between high end of mesopores (pores 2 to 50 nm) and low end of macropores (pores>50 nm), and in some embodiments, preferably between 25 nm and 35 microns.

To further reduce and control absorption rate and increase rigidity to ensure a user (e.g., dentist) can insert an absorbent insert all the way to the end of a root canal, the absorbent material (e.g., in sponge form) of the absorbent insert 10 shown in FIG. 3 is in a compressed state prior to use (i.e., prior to inserting into a tooth cavity).

FIGS. 5A to 5C schematically illustrates a compressing and cutting process for forming absorbent inserts 10 in connection with one embodiment of the present invention. In the illustrated embodiment, by applying pressure, wet sheets of absorbent material, e.g., sponge-like or sponge material are pressed into a single thin sheet of sponge-like material, dried and cut into the desired shape of the absorbent insert. For example, four sheets of 2.0 mm sponge (which may be in semi-compressed or non-compressed state) are stacked (total 8.0 mm total thickness), and compressed into a single sheet S having significantly less total thickness, e.g., 1.0 mm or less thickness. As shown in the sectional view of FIG. 5A, the sponge sheets 30 are compressed between a top pressing plate 20 and a base compression plate 21. Instead of compressing sheets of uniform absorbent materials (PVA/Cellulose/Hemicelluloses/hydrocolloid materials) into a uniform thickness sheet, pressing plate 20 and base compression plate 21 having unparallel opposing compression surfaces 22 and 23 are used to compress sheets 30 of the uniform absorbent materials into one uneven compressed dry sponge sheet with tapered cross section as shown in the sectional view of FIG. 5B. In this embodiment, the top pressing plate 20 has a compression surface 22 that is tapered in one direction (generally across the planar surface of the stack of material being compressed) relative to the opposing compression surface 23 of the base compression plate 21. In the illustrated embodiment, the top pressing plate 20 is tapered, and the base compression plate 21 is not tapered. Alternatively, the base compression plate 21 has a compression surface 23 that is tapered, and the top pressing plate 20 has a tapered compression surface 22 that is not tapered, or both the top pressing plate 20 and the base compression plate 23 may be tapered. In FIG. 5A, a compression force F is applied to the top pressing plate 20. Alternatively, a compression force F may be applied to the base compression plate 21, or compression forces may be simultaneously applied to both top pressing plate 20 and base compression plate 21.

The above compressing technique collapses and reduces pore size further and increase rigidity of the compressed sponge material. To compress the absorbent material, a pressure of, for example, 100 gram/square centimeters or higher is applied. When using sponge like material to make absorbent inserts, one can use already compressed sponge sheets 30 made of either cellulose/hemicellulose, hydrocolloids, or PVA. The type of compressed sponge sheet is rated by weight per square meter. For example, compressed cellulose sponge sheet may be rated 15 g per square meter. Another type of PVA compressed sponge sheet may be rated as near 400 g per square meter. Depending on absorbent rate of these materials used, the precompressed sheets 30 are compressed further as in FIGS. 5A and 5B with different pressure parameters to form a single compressed sheet S. With compressing (or when stamp molding process to be discussed later below), pressure from in the order of about 100 kg per square centimeters or higher may be applied.

FIG. 5B shows the sectional view of the tapered compressed sheet S, and FIG. 5C shows the perspective view of the tapered compressed sheet. The compressed sheet S is tapered in thickness, having a thicker edge 31 and a thinner edger 32. The tapered sheet S is then subject to cutting operation to obtain strips 35 and 36 of inserts that are sized for inserting into a tooth cavity (e.g., a prepared root canal space). Cutting may be performed by using a sharp blade, or by laser cuts, along the cut lines 33 and 34 shown in FIG. 5C. As illustrated, the cuts (e.g., laser cuts) may be parallel straight cuts 33 to provide tapered strips 35 having uniform width and tapered thickness, or the cuts 34 (e.g., laser cuts) may be angled in non-parallel (i.e., tapered) to obtain strips 36 that are tapered in both width and thickness. The strips 35 and 36 as shaped form absorbent inserts 10 similar to those illustrated in FIGS. 3 and 4 (with different cross-sections). The strips 35 and 36 so formed may be further finished (e.g., coating with a filler material as discussed below) to form absorbent inserts 10.

Laser beam can be used to cut the tapered sheet S into absorbent inserts as desired, either in a straight parallel cuts, or cuts at an angle to duplicate the cross-section taper of the sheet S to produce an absorbent insert having a taper. For both embodiments, the cross-section at axial locations of the inserts 10 so formed is generally rectangular or square. The laser beam should be at a lowest possible energy level and cutting must be done in a lowered temperature environment, between 0 and 6 degrees Celsius, to avoid burning of the compressed material in the sheet S. Test shown that slightly burning/melting of the material around the open pores by laser cutting would further reduce absorbent rate and increase rigidity, which at a more desired level could be an advantage.

The absorbent inserts in the form of an absorbent point for drying a root canal space has a generally slender longitudinal body, e.g., a generally rod shaped body (or a toothpick shaped body) or a tapered (e.g., conical) body, having a characteristic sectional dimension corresponding to a diameter/width/thickness that would fit into the space of a root canal. For example, the characteristic sectional dimension would be a diameter of a generally circular cross-section for an absorbent insert having a generally cylindrical longitudinal body, or the average diameter for an absorbent insert having a generally tapered, conical body. For an absorbent insert having a generally square cross-section (or the longer diagonal of a generally rectangular cross-section. For a typical tooth, the root canal diameter is less than 3 mm for a large molar, which is the largest tooth in a set of teeth of a person. The characteristic sectional dimension of the absorbent insert for a root canal should therefore be less than 3 mm, preferably less than 2 mm depending on the swelling/expansion rate of the insert. More particularly, such characteristic sectional dimension could be in the range of 0.15 mm to 1.2 mm at the tip end of the insert, and preferably in the range of 0.15 mm to 1.0 mm. For a tapered absorbent insert, the characteristic dimension of the smaller end should be ranging 0.15 mm to 1.0 mm, with a 2% to 4% taper.

If the sponge sheets made of known absorbent material is overly compressed by too long or too high a pressure, and/or at too high a temperature, the hydroxyl rich molecules and/or the pores in the sponge sheet could be destroyed. As a result, the compressed material loses its hydrophilic characteristic and capillary action effect. The above noted obstacles presented challenges that are overcome by the present invention. According to the present invention, the rigidity and absorbent rate of the novel absorbent inserts are controlled by adding organic or inorganic particles as filler can be incorporated into the absorbent material, so as to increase rigidity and to decrease absorbent rate to a desirable level. These filler materials can be (a) added to the absorbent material prior to forming the sponge sheet 30 in FIG. 5A, (b) added to the sponge sheet 30 prior to compressing process (e.g., between the layers of sponge sheets 30 in FIG. 5A), or (c) added as a final coating after absorbent inserts 10 have been compressed and shaped (e.g., after laser cutting in FIG. 5C). FIGS. 3 and 4 schematically illustrate illustrates the present of fillers Fr in the absorbent inserts 10 in the compressed state and in the swelled state. More specific examples of how fillers may be incorporated are as described below.

Examples of adding fillers to the absorbent material prior to compressing process include adding fillers to a mixture of starting raw materials before further compounding process and other processes to form the absorbent material into sponge sheet form. One or more filler materials may be added to gelatin form of absorbent material to make stiffer hydrocolloid material into sponge sheets. Further, one or more filler materials may be added to cellulose hemicellulose, polyvinyl alcohol (PVA), polyester, or similar materials before foaming/sponging process to form sponge sheets.

To add fillers to a sponge sheet prior to compressing process, filler material(s) can be added into a tank filled with distilled water as a suspension solution. After a sheet of sponge is formed, it is submerged into the filler suspension solution for a period of time while applying ultrasonic vibration to the tank, so that the sponge sheet soaks up/picks up fillers.

Sponge sheets 30 formed with fillers Fr can be placed through the above described compression process to obtain absorbent points 10 (e.g., with tapers) as illustrated in FIGS. 5A to 5C.

Fillers may be added to a compressed sponge sheet S, or directly to a compressed and shaped absorbent insert 10 (e.g., formed and shaped by any of the processes disclosed herein). One way to apply filler material(s) to compressed sponge sheet S may be by air etching (sand blasting) already compressed sponge sheet with filler materials. Similar process may be undertaken to apply filler material(s) to compressed and shaped absorbent inserts (e.g., after laser cutting discussed above in connection with FIG. 5C).

The amount of fillers added for intended purpose in this invention is preferably between 5% to 50% by weight of the base absorbent material, according to desired fluid absorbent rate and rigidity level. When using bonding agent as fillers, the preferred amount is 5% to 40% by weight of the base absorbent material.

In one aspect of the present invention, the fillers Fr are particles dispersed in the matrix of absorbent material of the absorbent inserts 10. The filler particles Fr may to some extent be chemically bound to the absorbent material, and/or interact with the absorbent material (e.g., oxidize), but the bulk of each filler particles in their modified form remain distinctive in the absorbent material, without dissolving as a solute in or compounding with the absorbent material. The filler particles are preferably bio-inert, which may be organic or inorganic, or a combination or mixture of both. The shape of the particles may be regular, irregular, symmetrical or non-symmetrical, having random or specific geometrical shapes (e.g., spherical, ellipsoidal, rhomboidal, disc, hollow or exotic shapes). The surface of the particles may be finished, e.g., polished, matte, or coated.

The characteristic size (or the statistical average size) of the particles is on the order of 100 microns or less. In one embodiment, the characteristic sizes of the fillers range from 25 nm (i.e., within mesopore size ranges) to 50 microns. The characteristic size of the particles does not have to be uniform. All particles may be generally or substantially the same size, or have random sizes within the prescribed size range. For generally spherical filler particles, size refers generally to the diameter of the particles; for filler particles of other 3D geometrical shapes that is not slender body, size refers to the average center sectional dimension; for filler particles having a generally slender body (e.g., a tube or rod shaped body), size refers to the largest dimension of the body). The characteristic size of the filler particles does not have to be uniform within the matrix material. All particles may be generally or substantially the same size, or have random sizes within the prescribed size range.

Examples of fillers include Titanium, Silica, Titanium Dioxide, and Zinc Oxide particles. Bonding agents may include Pectin and other bio-glue material such as Glutaraldehyde based compounds. Moreover, some of bonding agents may be air etched onto the surface of the absorbent material and be activated/cured (e.g., with a curing light).

The present invention provides further manufacturing processes to produce absorbent inserts suitable for root canals, with acceptable rigidity and absorbent rate. Some of the considerations for further manufacturing processes may include the following: (1) Some materials work better with injection molding processing such as hydrocolloid and polyester, or combination of both. Some materials such as cellulose, hemicelluloses, and polyester work better with rolling and spinning processing. Some materials such as polyvinyl alcohol work better with stamp molding processing. (2) The super absorbent materials can be used as original form without foaming process. Or they can be used as dry sponge texture via foaming processing. Or they can be used as compressed dry sponge texture. (3) For non-compressed dry sponge material, after absorbing fluid, the material volume does not change appreciably or change at negligible level. For compressed dry sponge, after absorbing fluid, its volume can increase by swelling to 1200% to 2100% its original compressed volume, depending on the extent of compression, type and amount of added filler and bonding agent, and the processing involved to form the final absorbent inserts. For purpose of the absorbent inserts of this invention and its clinical usage in respect to tooth cavities, the extent of expansion/swelling upon hydrating of the inserts shall not exceed 300% to 500%. (4) Traditional paper absorbent inserts are cone shaped with a single constant taper. It is desirable to configure absorbent inserts with multiple tapers along their longitudinal axis, to match root canal shapes prepared by multi-taper rotary NiTi files. (5)

Current absorbent paper point has round cross section and has a set of diameter sizes with defined tolerance range. Since compressed sponge can expand/swell by 300%-500% in volume after absorbing fluid, the requirement for round cross section, tapering, and tight size tolerance is no longer needed or critical. When a compressed sponge absorbent insert expands (swells) after absorbing fluid inside a root canal space, it will fill entire root canal space for better drying effect comparing to current paper based absorbent or non-compressed sponge based absorbent insert. The novel absorbent inserts can therefore have a body with no taper, a single fixed taper, or multiple tapers. The inventive compressed sponge based absorbent inserts can have a cross section in the shapes of circular, square, triangular, or other shape. The novel absorbent inserts can be produced in less number of available sizes to dentist, as compared to current practices with prior art paper cones, which come in a full range of available sizes needed to accommodate various root canal geometries.

In addition to forming absorbent points by pressing and cutting (discussed above in connection with FIGS. 5A to 5C), discussed below are additional processes for forming absorbent inserts having different absorbent material characteristics and for different final product/clinical needs.

(1) Injection Molding: Using a mold injection machine, pulp like material (e.g., hydrocolloid, cellulose or hemicellulose pulp) is injected into cavities of a mold to shape absorbent inserts. Reference is made to the injection molding technique disclosed in U.S. patent publication no. US2014/0315155A1, which discloses details of an injection molding system to form Gutta Percha dental root canal filling points. A similar injection molding system may be adapted for use to injection mold dental absorbent inserts disclosed herein, and the disclosure of US2014/0315155A1 is fully incorporated by reference herein.

Figure 6A:
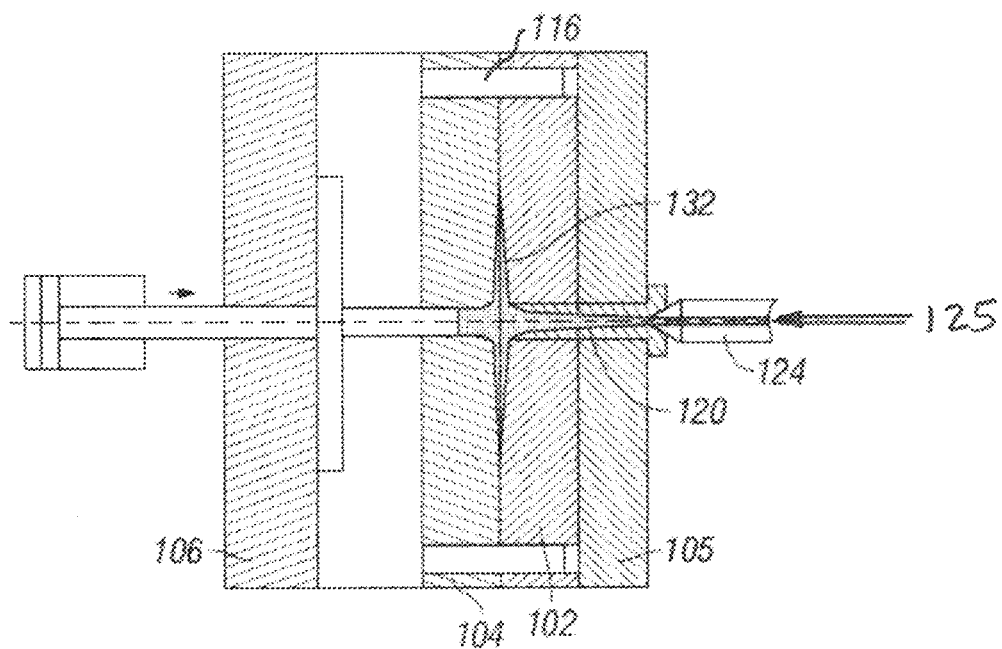
FIG. 6A is a schematic sectional view illustrating injection molding an absorbent insert in accordance with one embodiment of the present invention.

Referring to FIG. 6A, a split mold 100 has two mold halves 102 and 104 supported by frames 105 and 106. Each split mold halve 102/104 has a chamber defining the surface profile of part of the absorbent insert to be molded. The two halves 102 and 104 close together to make a full mold cavity 132. Pins 116 are provided for aligning the mold halves 102 and 104. One mold halve can be fixedly supported in the mold injection machine and the other mold halve is supported to move along a track with respect to the fixed mold halve, to open and close the mold. For injection of absorbent material 125, an injection nozzle 124 is butted against the outside of the mold frame 105, and material is injected into the mold cavity 132, through the pathway 120. US2014/0315155A1 discloses further improvements to the injection molding system, which may be adopted to injection mold absorbent points 10 in accordance with the present invention.

Figure 6B:
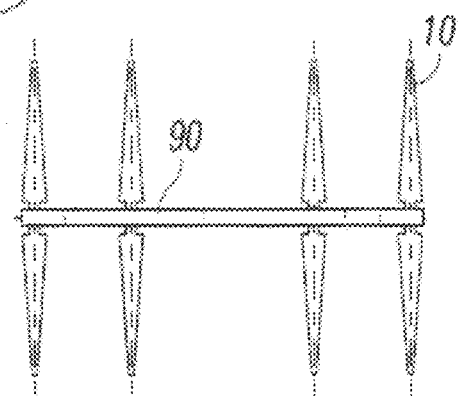
FIG. 6B is a schematic top view of a rack of molded absorbent inserts, in accordance with one embodiment of the present invention.

FIG. 6B is a schematic top view of a rack of molded absorbent point 10 in an overall molded structure, in accordance with one embodiment of the present invention. The absorbent inserts 10 are connected to a spine 90, resembling the shape of a rake, or a rack of absorbent inserts 10, so that all the absorbent inserts 10 can be collected and moved together in a cluster.

Given the different properties of pulp material used to make absorbent inserts as compared to the more viscous Gutta Percha material, appropriate pressure and temperature are adopted for injection molding of the pulp material herein. After molding/curing, absorbent inserts are made to precise dimension without worrying about fibers lodging deep inside a root canal system to become secondary infection sources. For example, hydrocolloid melts/softens at elevated temperature for injection molding (e.g., near 100 degrees Celcius), and hardens at 40 degrees Celcius, so the hydrocolloid essentially "cures" by temperature transition from the high injection molding temperature to low room temperature. A polymer can incorporate a light sensitive initiator, which after molding into shape, be subject to a curing light (e.g., laser or pure visible light (blue)). After curing, there will be little or no loose fibers (e.g., flailing fibers) at the surface of the absorbent point. This injection molding process will yield much cleaner absorbent insert than prior art paper points produced by a manual hand rolling process. Given the pressure of injection molding, the pulp material will be compressed after molding. This injection molding technique can produce single taper and multi-taper absorbent inserts, depending on the structure of the mold cavities.

When using injection molding process to make absorbent inserts with cellulose, hemicellulose or hydrocolloid fiber pulp suspension, injection molding machine system pressure is 35 kg per square centimeter. Sometimes, system pressure may be as high as 60 kg per square centimeter depending on amount of fiber and amount of fillers added to the pulp mixture.

If injection molding is carried out at too high a temperature and too high a pressure for a particular absorbent material, foamed sponge-like material is not suitable to be shaped into absorbent inserts with this injection molding technique. However, the absorbent inserts made with this technique are still able to absorb fluid by action of free hydroxyl radicals/groups and pores.

(2) Stamp Molding: All types of sponge materials mentioned above (cellulose, hemicellulose, PVA, polyester, hydrocolloid) may be stamp molded. However, stamp molding is particular useful for processing the material in foamed sponge form, in non-compressed and compressed state. Referring to FIGS. 7A to 7D, a split mold M for stamp molding is shown in accordance with one embodiment of the present invention. The split mold M includes two halves, a top halve 202 and a bottom halve 204, each having a series of cavities defined at the opposing surfaces of the top and bottom halves 202 and 204. More specifically, each mold halve 202/204 has a concave chamber 230 defining the surface profile of part of the absorbent insert 10 to be molded, which conforms to the shape of half an absorbent insert 10 along its longitudinal axis. The two halves 202 and 204 close together to make a full mold cavity 232. Pins 216 on the bottom mold halve 204 and complementary guide openings 217 in the top mold halve 202 are provided for aligning the mold halves 202 and 204. One mold halve 202/204 can be fixedly supported in the stamp molding machine and the other mold halve is supported to move along a track with respect to the fixed mold halve, to stamp press a sheet of absorbent material 225 by opening and closing the mold M.

Figure 7A:
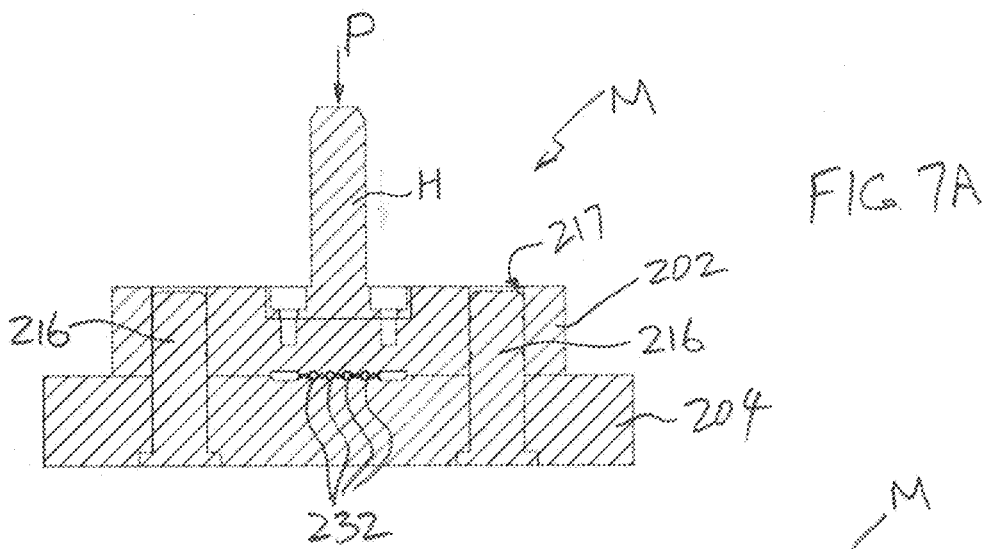
FIG. 7A is a schematic sectional of the stamp molding mold taken alone line 7A-7A in FIG. 7B.
Figure 7B:
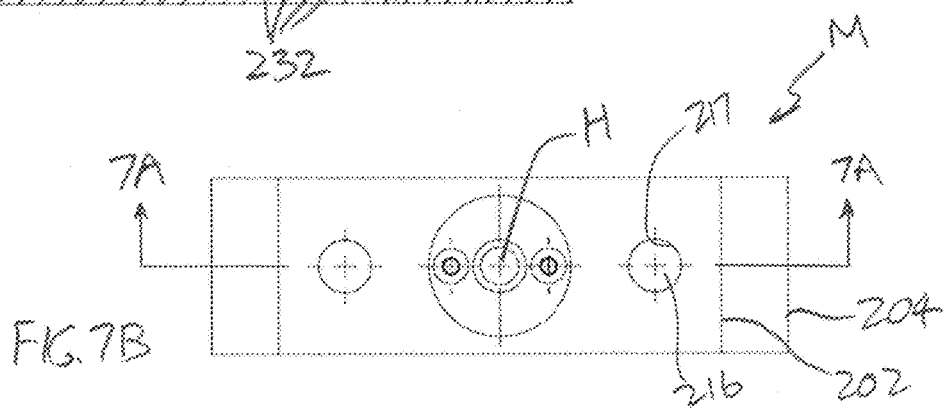
FIG. 7B is a schematic top view of the stamp molding mold in FIG. 7A.
Figure 7C:
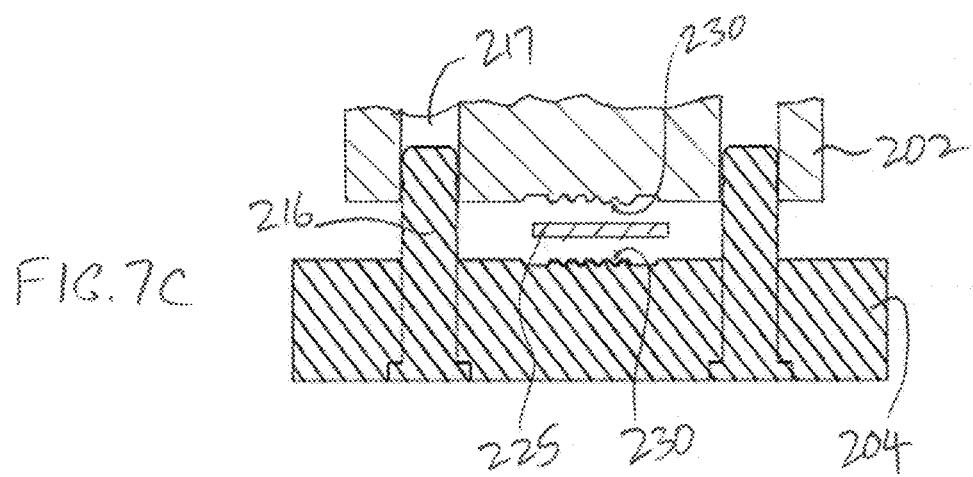
FIG. 7C is a schematic sectional view illustrating the stamp molding mold in FIG. 7A receiving a sheet of absorbent material between its mold halves for stamping operation.
Figure 7D:
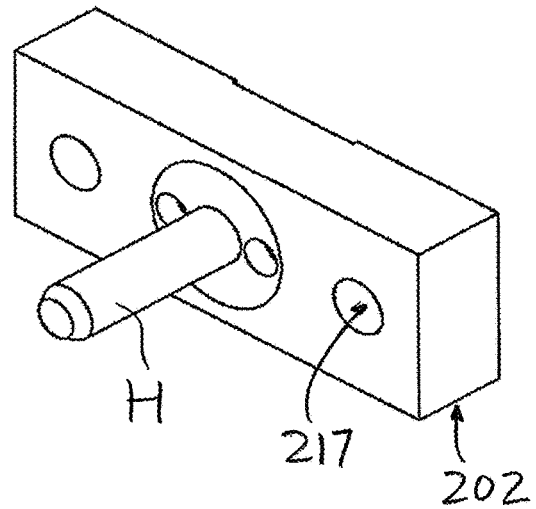
FIG. 7D is a schematic perspective view of the top mold halve in FIG. 7A.
Figure 7E:
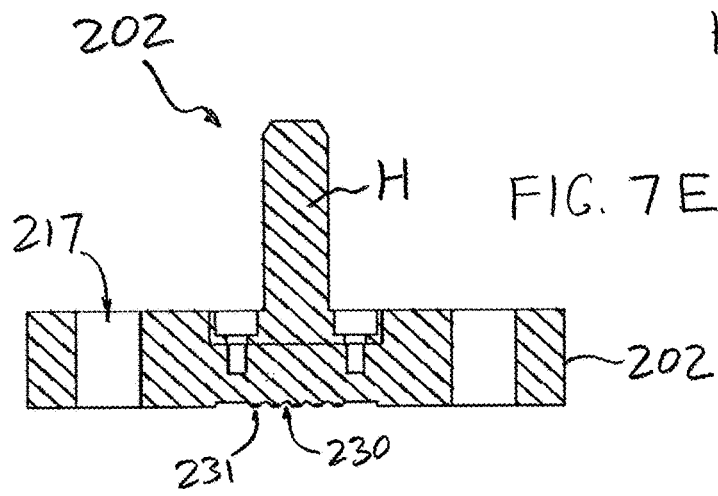
FIG. 7E is a schematic sectional view of the top mold halve taken along line 7E-7E in FIG. 7F.
Figure 7F:
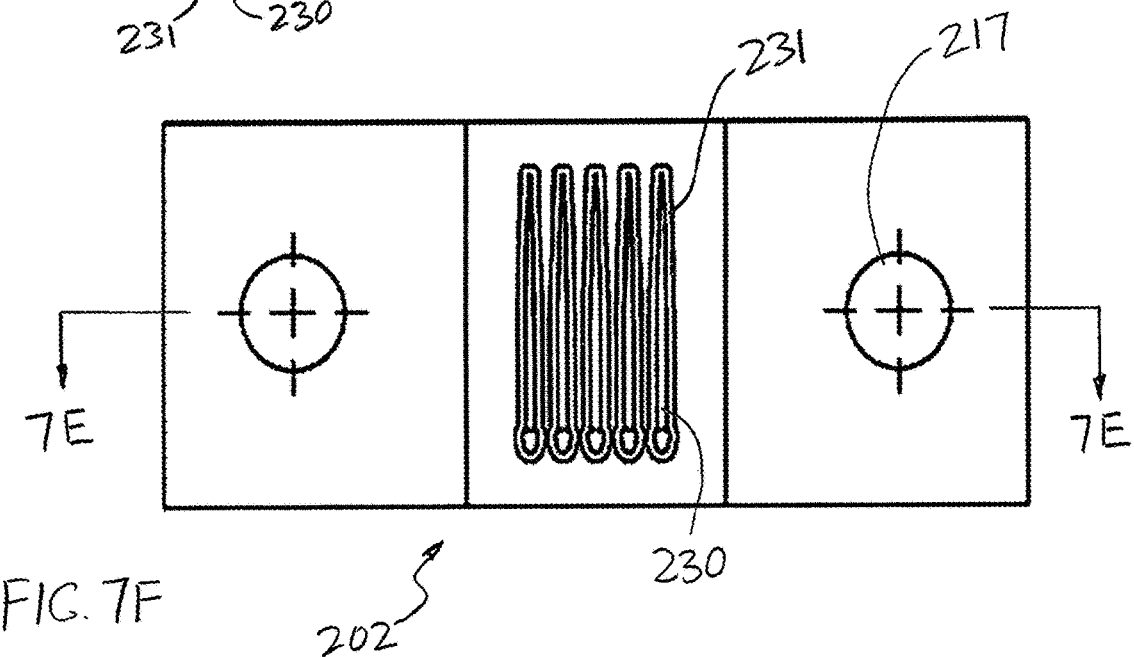
FIG. 7F is a bottom view of the top mold halve showing the mold chambers.

In FIG. 7C, stamping force/pressure P is applied after the sheet of absorbent material 225 of predetermined thickness and rigidity is placed between the opposing surfaces of the top halve 202 and bottom halve 204 of the split mold M. The top halve 202 and the bottom halve 204 of the mold M are advanced relatively towards each other at a controlled speed to slowly apply pressure P on the sheet of material 225 to compress it and mold individual longitudinal absorbent inserts 10 within pairs of opposing mold cavities. In the illustrated embodiment, the top mold halve 202 may be lowered towards the bottom mold halve 204 by applied pressure P to the handle H, or alternatively the bottom mold halve 204 may be raised towards the top mold halve 202, or both the top and bottom mold halves 202 and 204 may be moved towards each other, to assert the desired pressure P against the sheet of absorbent material 225. The stamping pressure P applied reduces pore sizes in the sheet of absorbent sponge, but not to destroy all the pores in the absorbent sponge.

As illustrated, each half mold cavity (in both the top mold half and bottom mold half) has a sharp edge 231 around each chamber 230, which mates with a similar sharp edge 231 around the chamber 230 of the opposing mold halve. At the end of the compression cycle in the stamp molding process, a quick punch motion closing the upper mold halve 202 and bottom mold halve 204 (e.g., with the top mold halve 202 imparting a quick punch motion on a stationary bottom mold halve 204) would finally close all the mold cavities 232 between the mold halves, and the sharp chamber edges 231 serve as a cutter to separate individual absorbent inserts 10 and shear off excess material outside the mold cavities 232.

This injection molding technique can produce single taper and multi-taper absorbent inserts, depending on the structure of the mold chambers 230.

If the mold cavities 232 are shaped to stamp mold absorbent inserts 10 having a taper, the portion closer to the smaller end of the absorbent inserts 10 will be subject to higher stamp molding pressure given the less space between the chambers 230 of the mold halves 202 and 204, and hence would have a denser material and finish, and smaller pores. This will produce more rigidity to the absorbent inserts 10 so formed to compensate for a smaller diameter near the smaller end of the absorbent inserts.

Further, the mold chambers 230 may be linked to allow stamp molding a rack of connected absorbent inserts 10, similar in structure as the structure shown in FIG. 6B. This facilitates handling of several molded absorbent inserts 10.

The sheet of absorbent material 225 used for the stamp molding process may be uncompressed, or precompressed, subject to further compression by the stamp molding process. Further, instead, the sheet of absorbent material 225 may correspond to the sheet S obtained by compression using the process discussed above in connection with FIGS. 5A and 5B. That is, the absorbent material 225 may be a sheet S of sponge material which may be a tapered sheet or a sheet of uniform thickness, compressed from multiple sponge sheets 30 obtained by compression in FIGS. 5A and 5B. In this case, instead of the cutting process in FIG. 5C, the stamp molding process is adopted for cutting and also shaping in a single process step.

Figure 8A:
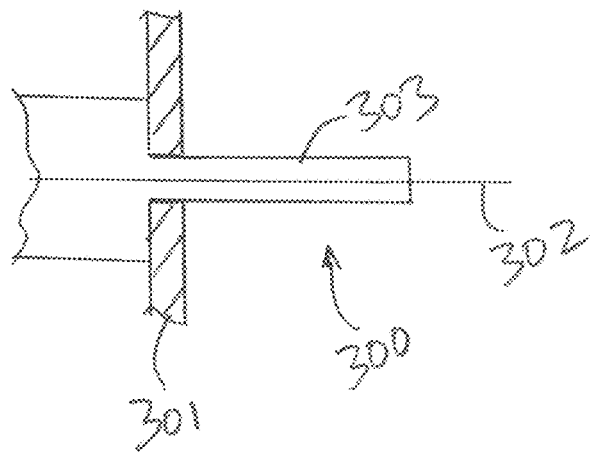
FIG. 8A is a schematic sectional view illustrating extrusion of an absorbent material, in accordance with one embodiment of the present invention.
Figure 8B:
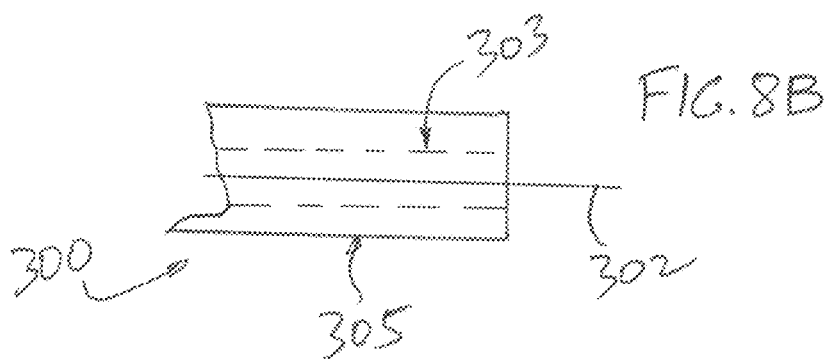
FIG. 8B is a schematic sectional view of the rope being subjected to foaming procedure.
Figure 8C:
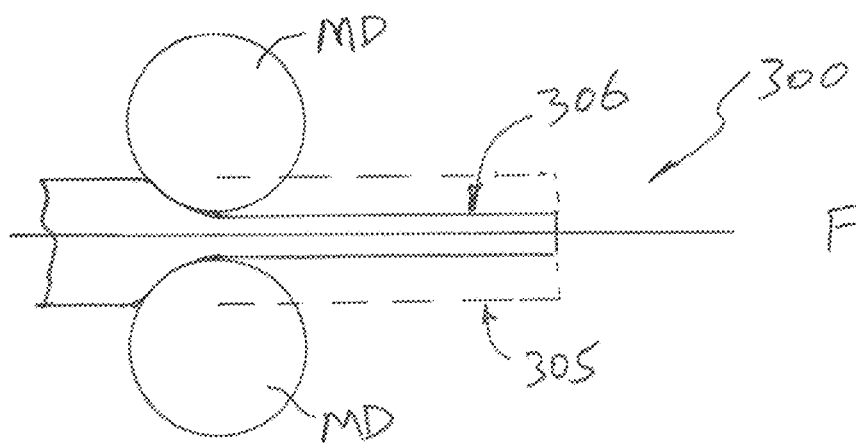
FIG. 8C is a schematic sectional view of the rope in FIG. 8B being subject to further compression, in accordance with another embodiment of the present invention.
Figure 8D:
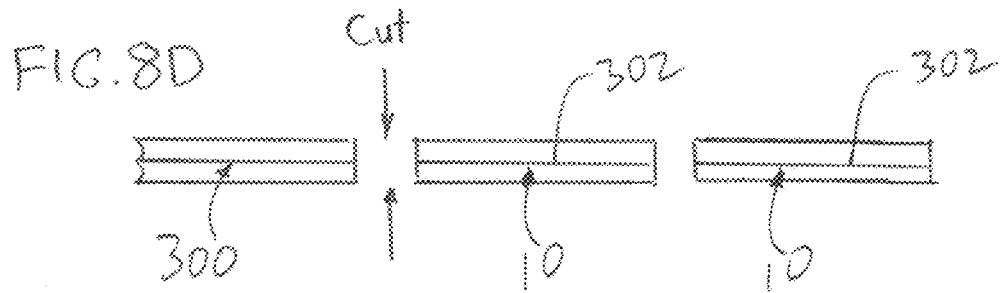
FIG. 8D is a schematic view of cutting the rope to form individual absorbent inserts.

(3) Extrusion: All types of sponge materials mentioned above (cellulose, hemicellulose, PVA, polyester, hydrocolloid) may be suitable for extrusion. The above-mentioned materials have low enough viscosity, so they only require minimal extruding pressure to form a thin rope 300 of material. Preferably, as schematically illustrated in FIG. 8A, extrusion of the sponge material 303 is undertaken through an extrusion die 301, using a core filament 302 (much like the insulative plastic coating of an electrical wire is extruded with the wire as a core element). The core filament 302 can be made of thin gauge nylon or stainless steel. The absorbent material 303 can have foaming agent premixed into it and foam expansion rate can be regulated as 1.5× to 3×. For example, if the final absorbent insert 10 is to have a diameter of 0.20 mm, one can use the core filament of 0.04 mm diameter coated with a thick layer of 1× foam expansion rate absorbent material. By subjecting the filament 302 and coating of material 303 to extrusion through an extrusion die 301, a rope 300 of 0.12 mm diameter is formed, with the 0.04 mm filament and a 0.04 mm thick coating of absorbent material 303 (total of 0.08 mm in absorbent material in cross section). In FIG. 8B, the rope is then subject to foaming in a foaming chamber to form a sponge like coating 305 over the filament. The 1× foam expansion in the absorbent material results in a 0.08 mm thick coating 305 over the filament (thus a total of 0.16 mm in sponge material over the 0.04 mm filament, totaling 0.20 mm in final total diameter of the rope). The original size of the coating of material 303 prior to foaming is shown in dotted line in FIG. 8B. Referring to FIG. 8C, if desired, by choosing an absorbent material 303 with even a higher foam expansion rate, a rope 300 having the foam expanded absorbent material 305 can be subject to pressure/compression, for example, by rolling the rope between mandrels MD or tight winding and pressing onto a mandrel, or by subjecting the rope to a further extrusion step, to reduce the overall dimension of the extruded rope 300 to the desired diameter at 306. The original size of the foamed expanded material 305 is shown in dotted lines in FIG. 8C. Finally, in FIG. 8D, the rope 300 is then cut into desired length, to form absorbent inserts 10. Alternatively, finished ropes 300 of different diameters may be manufactured (by using different foaming factor) and made available to a dentist, who can then decide on the particular diameter(s) of ropes 300 to use for a dental procedure, and she can cut absorbent inserts having the desired length(s) and diameter(s) for use.

Figure 9A:
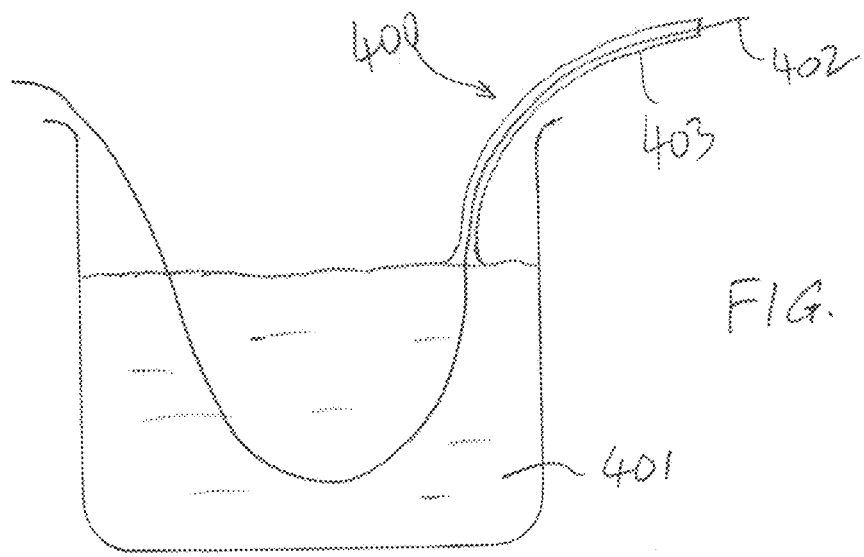
FIG. 9A is a schematic sectional view illustrating liquid molding/dip molding of an absorbent material, in accordance with one embodiment of the present invention.
Figure 9B:
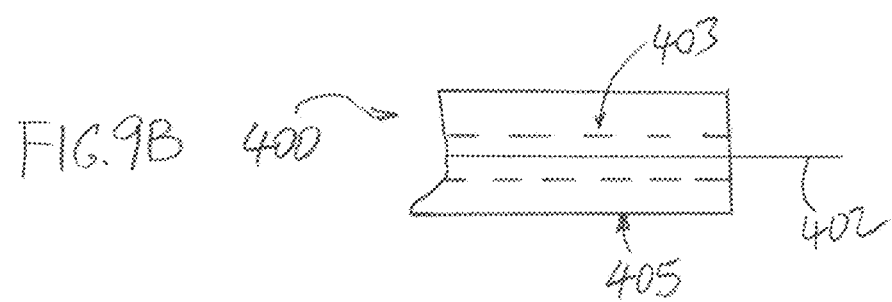
FIG. 9B is a schematic sectional view of the rope being subjected to foaming procedure.
Figure 9C:
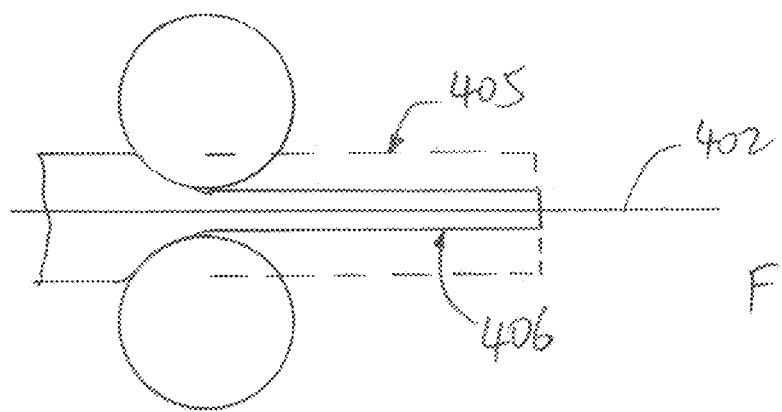
FIG. 9C is a schematic sectional view of the rope in FIG. 9B being subject to further compression, in accordance with another embodiment of the present invention.
Figure 9D:
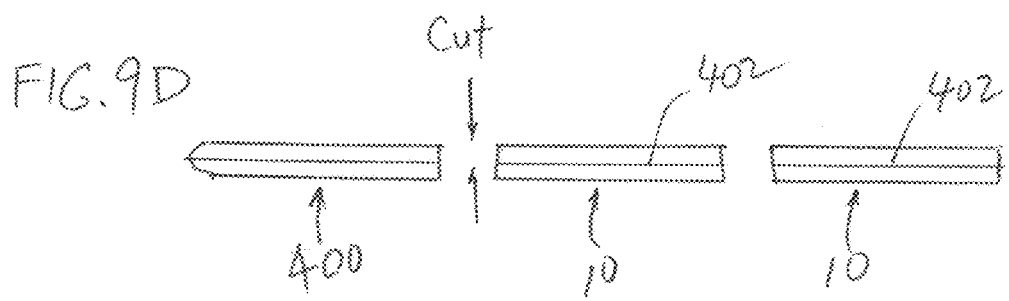
FIG. 9D is a schematic view of cutting the rope to form individual absorbent inserts.

(4) Liquid molding (dip molding): Referring to FIGS. 9A to 9C, using above extruding technique as an example, a pool of liquified absorbent material 401 having a predetermined expansion rate, and with foaming agent added, is prepared with desired viscosity under consistent temperature control. Each of the above mentioned absorbent material has its own melting temperature without destroying free hydroxyl radicals/groups. A filament 402 is run through this pool of absorbent material 401 at a controlled speed to form a coating of absorbent material 403 over it with a desired thickness to form a rope 400. In FIG. 9B, the rope 400 is then subject to foaming in a foaming chamber to form a sponge like coating 405 over the filament. The original size of the coating of material 403 prior to foaming is shown in dotted line in FIG. 9B. Referring to FIG. 9C, if desired, by choosing an absorbent material 403 with even a higher foam expansion rate, a rope 400 having the foam expanded absorbent material 405 can be subject to pressure/compression, for example, by rolling the rope 400 between mandrels MD or by winding and pressing onto a mandrel to reduce the overall dimension of the extruded rope 400 to the desired diameter at 406. In the alternate or in addition, the rope 400 may be subject to a further extrusion step such as the earlier extrusion process discussed above, to obtain a finished rope having the desired diameter 406. The original size of the foamed expanded material 405 is shown in dotted lines in FIG. 9C. Finally, in FIG. 9D, the rope 300 is then cut into desired length, to form absorbent inserts 10. Alternatively, finished ropes 400 of different diameters may be manufactured (by using different foaming factor) and made available to a dentist, who can then decide on the particular diameter(s) of ropes 400 to use for a dental procedure, and she can cut absorbent inserts 10 having the desired length(s) and diameter(s) for use.

Figure 10A:
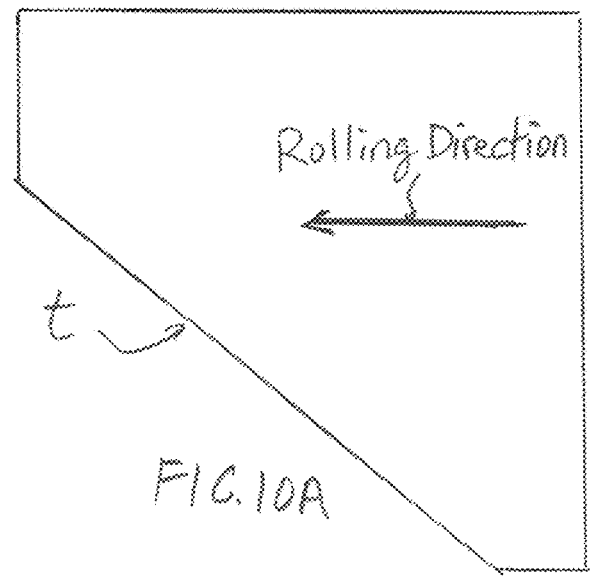
FIG. 10A is a schematic top view of a sheet of absorbent material cut and shaped for rolling into an absorbent insert having a single taper, in accordance with one embodiment of the present invention.
Figure 10B:
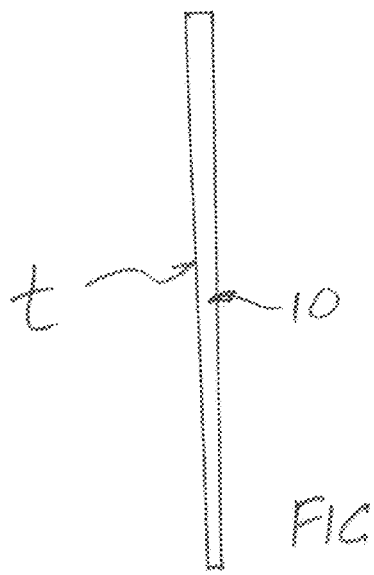
FIG. 10B is a schematic sectional view of single-tapered absorbent insert rolled from the sheet shown in FIG. 10A, in accordance with one embodiment of the present invention.
Figure 10C:
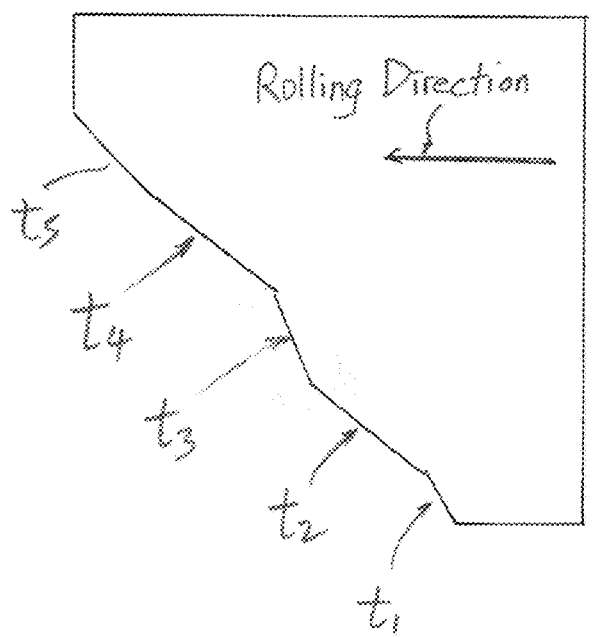
FIG. 10C is a schematic top view of a sheet of absorbent material cut and shaped for rolling into an absorbent insert having multiple tapers, in accordance with one embodiment of the present invention.
Figure 10D:
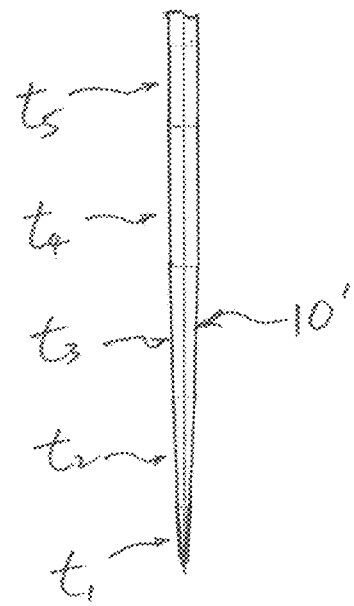
FIG. 10D is a schematic sectional view of multi-tapered absorbent insert rolled from the sheet shown in FIG. 10C, in accordance with one embodiment of the present invention.

(5) Rolling: All above mentioned materials can be made into a very thin, soft, slightly foamed sheets, which are precut into a shape (see FIGS. 10A and 10C) such that when the sheet is rolled in the direction as shown, a body having a desired taper(s) can be formed. Using a rolling jig (e.g., similar to a rolling jig for prior art paper absorbent points), the precut sheet can be rolled under pressure into a single or multi-tapered absorbent insert, which resultant compression of the insert. FIG. 10A shows a sheet 500 precut with a geometry to be rolled to form a single tapered absorbent insert (having a single taper t shown in FIG. 10B, which is similar to the geometry of the tapered insert 10 shown in FIG. 4A). FIG. 10C shows a sheet 500' precut with a geometry to form a multi-tapered absorbent insert 10', having the geometry schematically shown in FIG. 10D (five different tapered sections t1 to t5).

As shown in FIG. 10C, in comparison to the absorbent insert 10 in FIG. 4A, which has a single taper angle for substantially its entire length, the multi-taper absorbent insert 10' in FIG. 10C has a different taper angle for different longitudinal sections along its length. To this date, while clinicians use Progressive Tapering File system, no one thought of providing multi-taper absorbent inserts to complement such multi-taper file system. In one embodiment, the multi-taper absorbent insert 10' has a generally axisymmetric conical structure, wherein at least a section along the length of the absorbent insert 10' has a tapered structure, wherein the taper angle varies progressively in the axial direction to result in a multi-taper or variable taper conical structure. In one embodiment, the taper angles vary in small, discrete incremental steps along the length of the point, thus forming a structure having adjoining conical sections having different and discretely varying tapers at different axial sections along the length. The diameter of each diametric section along the longitudinal axis of the body of the absorbent insert 10' is substantially circular between the small tip end and the large end.

In further embodiments, the tapers may vary continuously, gradually and smoothly along the length of the cone to form a gradual arcuate or curved surface profile in the axial direction representing continuously varying tapers. The axial lengths of at least two adjoining axially connected conical sections may be different. Further, in other embodiments, the taper configurations for multi-tapered absorbent point can be any combination of large taper, small taper, zero taper, increasingly varying, decreasingly varying, randomly varying, progressively varying, or regressively varying.

As discussed above, compressed PVA/Cellulose/Hemicelluloses/hydrocolloid sponge material can be used to make new types of root canal absorbent insert.

In another aspect of the present invention, the absorbent insert is applied as an absorbent point that also serves as a substrate of an applicator for medication to be applied to a tooth cavity (e.g., a root canal, a pulp chamber). The absorbent insert is impregnated with medication, which is released into the tooth cavity as the absorbent material absorbs fluid in the tooth cavity.

Infection inside root canal system is difficult to treat and often spread into surrounding bone tissue. Systemic use of antibiotic agents tends not to work as effectively as targeting infection in other part of body. Part of the reasons for this phenomenon is anatomic feature of tooth root canal structure—lack of blood supply. As a result, antibacterial agents and other reagents are directly placed deep inside root canal space as interim treatment, and patients are requested to return to the dental clinic multiple times to change medication/reagent before root canal treatment can be completed. Applying medication/reagent deep into root canal space is difficult with current methodology—using paper absorbent as an applicator dipping into a reagent in paste form and coating the reagent into the root canal space. Paper point gets soft with coated paste and often cannot reach deep into the root canal space.

Figure 11A:
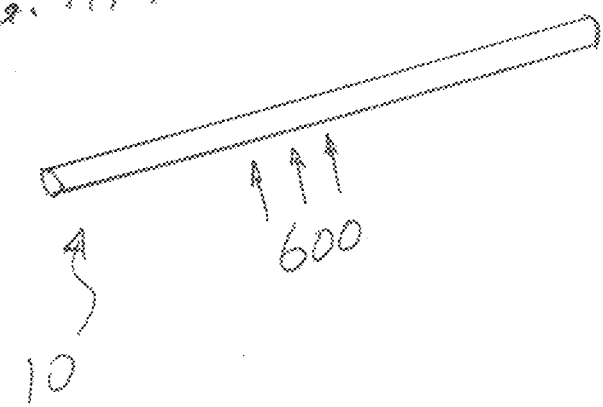
FIG. 11A is a schematic view of an absorbent insert deposited with a medical agent, in accordance with one embodiment of the present invention.
Figure 11B:
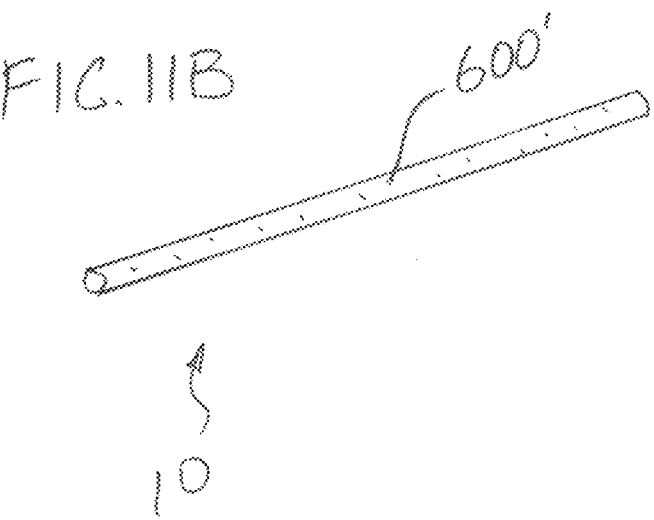
FIG. 11B is a schematic view of an absorbent insert impregnated with a medical agent, in accordance with another embodiment of the present invention.

The novel inventive absorbent inserts discussed above can be placed and left inside a root canal space for an extended period, e.g., up to 14 days. Referring to FIG. 11A, for example, by using air etching technique, a coating 600 of medical agents (e.g., antibiotics, medications, etc.) may be formed onto the surface of the inventive absorbent insert 10 (which may be formed by any of the above described process). Once these pre-medicated absorbent inserts 10 are placed deep inside the root canal space and start to soak up blood and other fluids in the space, the surface coated medical agents will be released and more effectively counter bacterial infections and/or achieve other health effects. Commonly used agents are Calcium Hydroxide, time release formula Minocycline HCL, Chlorohexidine, white Betadine, and other pain control agents. The desired concentration of these agents is measured by percentage of weight. For treating young teeth yet in root development stage and repairing bone lesions, growth factors and bio-inductive agents such as Hydroxyapatite (HA) can also be coated onto the surface of this new generation absorbent inserts and placed into root canal space for up to eight weeks at a time.

Alternatively, medical agents 600' may be impregnated into the absorbent material of the absorbent insert 10 prior to or post final forming/shaping by e.g., any of the above described processes.

While the present invention has been described above in connection with the illustrated embodiments, the scope of patent invention covers all possible present and future variations and improvements that is apparent from the disclosure above. While the invention has been particularly shown and described with reference to the preferred embodiments, it will be understood by those skilled in the art that various changes in form and detail may be made without departing from the spirit, scope, and teaching of the invention. Accordingly, the disclosed invention is to be considered merely as illustrative and limited in scope only as specified in the appended claims.

I claim:

1. A method of making an absorbent insert for absorbing fluid in a root canal, comprising forming a body in a pre-compressed state comprising a matrix of absorbent material, wherein the body is in the pre-compressed state prior to the insert being inserted into the root canal, and wherein the matrix of absorbent material swells upon absorbing fluid after the body in the pre-compressed state has been inserted the root canal,
   wherein the forming step comprises:
     providing a sheet of absorbent material;
     compressing the sheet of absorbent material to form a compressed sheet; and
     cutting and shaping the compressed sheet of absorbent material to form at least one insert; and
   wherein the cutting and shaping step comprises:
     providing complementary split mold halves, which together define at least a cavity corresponding to the shape of the body of the insert;
     placing the compressed sheet of absorbent material between the split mold halves; and
     stamping the compressed sheet with the split mold halves to form the body of the insert, wherein the absorbent material is in the pre-compressed state after stamping.

2. The method as in claim 1, wherein the absorbent material comprises a sponge material.

3. The method as in claim 2, wherein the sponge material comprises at least one of polyvinyl alcohol (PVA), polyester, cellulose, hemicellulose, and hydrocolloid.

4. The method as in claim 2, wherein the body further comprises a filler dispersed in the sponge material.

5. The method as in claim 4, wherein the filler comprises at least one of Titanium, Silica, Titanium Dioxide, and Zinc Oxide particles.

6. The method as in claim 1, wherein the body has a sectional dimension less than 2 mm before absorbing fluid.

7. The method as in claim 6, wherein the body is shaped with a longitudinal structure.

8. The method as in claim 7, wherein the longitudinal structure comprises a predefined tapered structure terminating in a tip end that is smaller than rest of the longitudinal structure.

9. The method as in claim 8, wherein the tapered structure comprises a plurality of tapered sections along an axial direction of the longitudinal structure of the body, wherein at least two of the tapered sections have different tapers along the axial direction, thereby defining a multi-tapered structure.

10. The method as in claim 1, wherein the body further comprises a medical agent, wherein the medical agent is released when the absorbent material is exposed to fluid in the root canal.

11. The method as in claim 10, wherein the medical agent is disposed at least at or near an exterior surface of the body.

12. The method as in claim 11, wherein the medical agent is coated onto the exterior surface of the body.

13. The method as in claim 10, wherein the medical agent is at least impregnated in the absorbent material.

14. The method as in claim 10, wherein the medical agent comprises at least an active ingredient for treatment of root canal, to provide treatment effect of at least one in following group: therapy, treatment, healing, curative, remedial, restorative, tonic, reparative, corrective, antibiotic, anesthetic, disinfect, anti-inflammatory, pain relief.

15. The method as in claim 10, wherein the medical agent comprises at least one agent in following group: of a healing agent, a curative agent, a remedial agent, a restorative agent, a tonic agent, a reparative agent, a corrective agent, an antibiotic agent, an anesthetic agent, a disinfecting agent, a blood clotting agent, a steroidal agent, a hormonal agent, anti-inflammatory agent, a pain-relieving agent.

16. The method as in claim 1, wherein the forming step further comprises:
   providing the sheet of absorbent material in the form of a plurality of wet sheets of absorbent material;
   compressing the sheet of absorbent material in the form of the wet sheets of absorbent material to form the compressed sheet of absorbent material; and
   cutting and shaping to form at least a body of the absorbent insert from the compressed sheet.

17. The method as in claim 16, wherein compressing step comprises:
   providing complementary top and base pressing plates; and
   compressing the plurality of wet sheets of absorbent material between the top pressing plate and the base pressing plate to form the compressed sheet of absorbent material.

18. The method as in claim 17, wherein the top pressing plate and the base pressing plate have unparallel opposing compression surface and compressing the wet sheets of absorbent material to form the compressed sheet with a tapered cross section.

* * * * *